United States Patent [19]

Schmidt

[11] Patent Number: 4,484,013

[45] Date of Patent: Nov. 20, 1984

[54] PROCESS FOR COPRODUCTION OF ISOPROPANOL AND TERTIARY BUTYL ALCOHOL

[75] Inventor: Robert J. Schmidt, Rolling Meadows, Ill.

[73] Assignee: UOP Inc., Des Plaines, Ill.

[21] Appl. No.: 567,205

[22] Filed: Dec. 30, 1983

[51] Int. Cl.$^3$ .................... C07C 29/04; C07C 31/10; C07C 31/12

[52] U.S. Cl. ................................. 568/899; 568/895; 568/896; 568/897; 568/898; 568/900; 568/901

[58] Field of Search ................................ 568/895–901

[56] References Cited

U.S. PATENT DOCUMENTS

| | | | |
|---|---|---|---|
| 2,173,187 | 9/1939 | Tanner | 568/896 |
| 3,328,469 | 6/1967 | Spector et al. | 260/641 |
| 3,328,471 | 6/1967 | Krönig et al. | 260/641 |
| 3,849,082 | 11/1974 | Kozlowski et al. | 44/56 |
| 3,994,983 | 11/1976 | Webers et al. | 260/641 |
| 4,281,206 | 7/1981 | Brandes et al. | 568/396 |
| 4,284,831 | 8/1981 | Okumura et al. | 568/899 |
| 4,307,257 | 12/1981 | Sada et al. | 568/899 |
| 4,327,231 | 4/1982 | Okumura et al. | 568/896 |
| 4,340,769 | 7/1982 | Brandes et al. | 568/899 |
| 4,376,225 | 3/1983 | Vora | 585/659 |
| 4,381,417 | 4/1983 | Vora et al. | 585/655 |
| 4,393,256 | 7/1983 | Schmidt | 568/907 |
| 4,423,251 | 12/1983 | Pujado et al. | 568/899 |

FOREIGN PATENT DOCUMENTS 0042252 12/1981 European Pat. Off. ............ 568/895
1018201 10/1952 France .................... 568/895

OTHER PUBLICATIONS

Hydrocarbon Processing, Nov. 1967, p. 194.
Hydrocarbon Processing, Nov. 1967, vol. 46, No. 11, p. 195.
Hydrocarbon Processing, Nov. 1981, p. 173.
Hydrocarbon Processing, Apr. 1982, pp. 171–174, "$C_2/C_5$ Dehydrogenation Updated" by B. V. Vora and T. Imai.
Oil & Gas Journal, Nov. 10, 1980, pp. 191–197, "Catalytic LPG Dehydrogenation Fits in '80's Outlook" by R. C. Berg, B. V. Vora, J. R. Mowry.

Primary Examiner—J. E. Evans
Attorney, Agent, or Firm—William H. Page, II; John F. Spears, Jr.

[57] ABSTRACT

A process is disclosed for the production of isopropanol and tertiary butyl alcohol from $C_3$ and $C_4$ hydrocarbons. The preferred embodiment of the invention comprises dehydrogenation of paraffins and direct hydration of the resulting olefins. Fractional distillation steps are employed between the dehydrogenation and dehydration zones and in the recycle stream to recover unconverted hydrocarbons leaving the hydration zone. This accommodates different hydration rates and prevents the passage of propylene into the dehydrogenation zone. In an alternative embodiment, the feed stream comprises olefins and is fed to the fractionation system. The dehydrogenation zone may be deleted from this embodiment.

20 Claims, 1 Drawing Figure

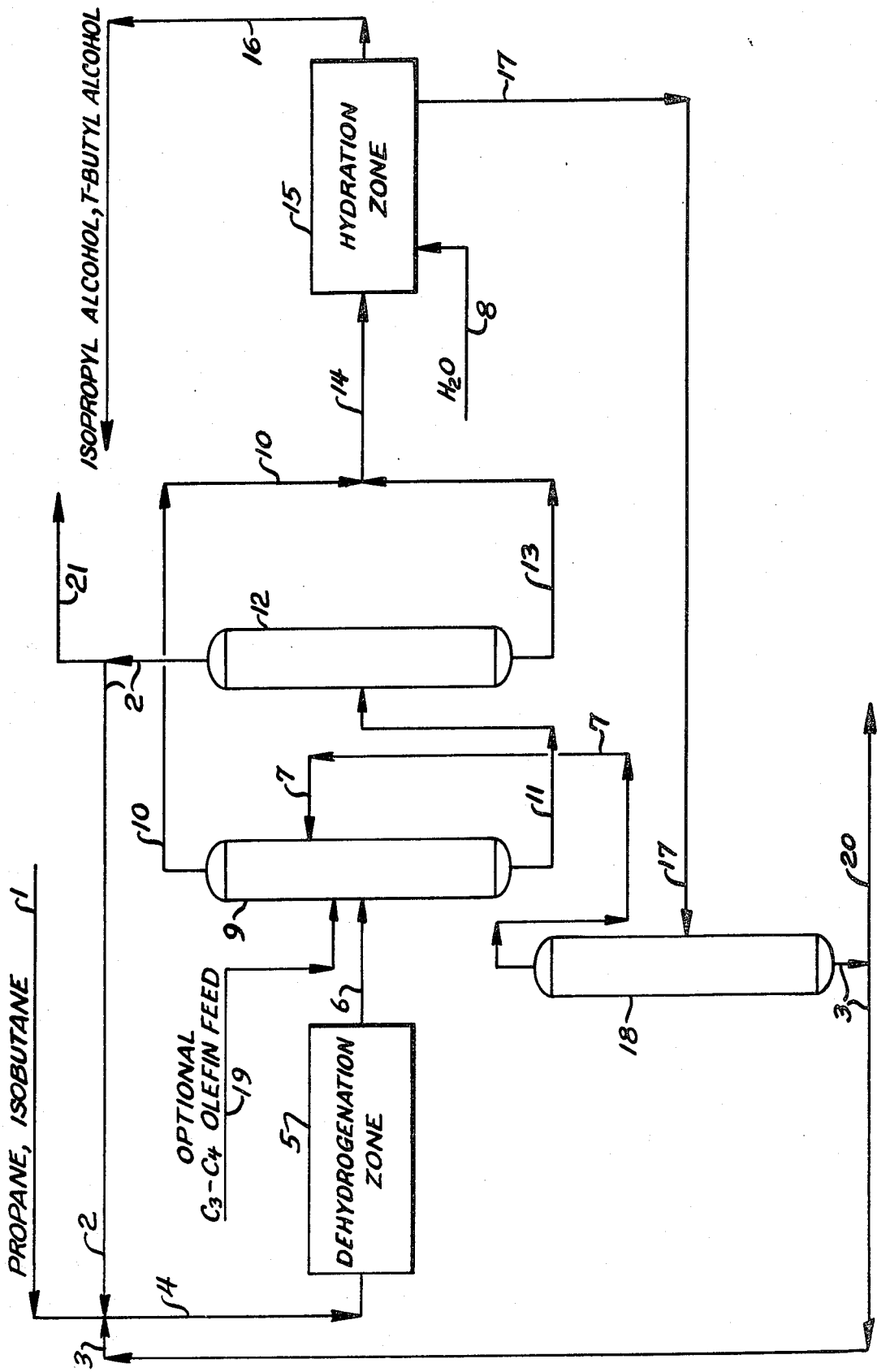

PROCESS FOR COPRODUCTION OF ISOPROPANOL AND TERTIARY BUTYL ALCOHOL

FIELD OF THE INVENTION

The invention is a hydrocarbon conversion process. More specifically, the invention is an integrated process for producing aliphatic alcohols from aliphatic hydrocarbons through dehydrogenation followed by direct hydration of the resulting olefinic hydrocarbons. The preferred feedstock is a mixture of propane and isobutane, which is converted to isopropanol and tertiary butyl alcohol. The invention directly relates to various fractional distillation steps employed within the process to selectively recycle propane and isobutane to the dehydrogenation zone.

INFORMATION DISCLOSURE

The synthetic production of isopropyl alcohol is a well established commercial industry. Among the earliest processes for the production of isopropyl alcohol were the so-called indirect hydration processes. A basic form of this type of process comprises the reaction of the olefin with sulfuric acid of various concentrations to produce alkylsulfates which are then hydrolyzed to produce the corresponding alcohols. The process flow illustrated on page 194 of the November 1967 issue of *Hydrocarbon Processing* is believed representative of this type of isopropyl alcohol synthesis process. This type of process has various problems such as the corrosiveness of the sulfuric acid and various compounds present in the process, costly acid reconcentration, high chemical consumption, significant by-product formation and a generally complicated process flow. These shortcomings have prompted the development of the so-called direct hydration processes.

In the direct hydration process, a feed olefinic hydrocarbon such as propylene is directly reacted with water to produce the product alcohol. One early form of this direct hydration is described in U.S. Pat. No. 3,328,469 (Spector et al.). This patent teaches that the isopropyl alcohol may be recovered from a vapor phase reactor effluent by scrubbing the effluent in a packed tower with water. The resultant aqueous isopropyl alcohol solution is withdrawn from the bottom of the scrubber and fed to a distillation zone. In a first fractionation column, water is separated as a bottoms fraction. The overhead, comprising an azeotropic mixture of isopropyl alcohol, is then sent to a second distillation column for the removal of impurities such as propylene and isopropyl halides. For the manufacture of anhydrous isopropyl alcohol, the reactor effluent is condensed and subjected to a phase separation procedure. An isopropyl alcohol-containing phase is removed from the separation zone and passed into a distillation zone. The recovery of isopropyl alcohol by fractionation in a similar direct hydration process is illustrated in the diagram presented at page 195 of the November 1967 issue of *Hydrocarbon Processing*.

A flow diagram of the reaction section and the fractionation section of a contemporary process for the production of isopropyl alcohol is presented at page 173 of the November 1981 issue of *Hydrocarbon Processing*. In this flow scheme, the propylene and water are passed into a reactor, with water also being injected at intermediate points along the length of the reactor. The reactor effluent is a liquid phase stream which is passed into a vapor-liquid separation zone. Vapors from this separation zone are passed to a propylene recovery zone in which the propylene is separated from propane. The liquid phase from the separation zone is charged to a distillation column from which the diisopropyl ether by-product is removed overhead. The bottoms of the first column are charged to a second column in which isopropyl alcohol is taken overhead as an aqueous azeotropic mixture. Dehydration of the azeotropic mixture is carried out using benzene as an entrainer. Water removed as a bottoms product from the second column is internally recycled within the process.

The current development work in the area of direct hydration catalyst appears to be centered on the use of ion exchange resins. A particularly preferred type of such resin is described in U.S. Pat. No. 4,340,769 (Brandes et al.). U.S. Pat. Nos. 3,994,983 (Webers et al.) and 4,281,206 (Brandes et al.) are pertinent for their teaching of the reaction zone configurations, conditions, and techniques which may be employed for the direct hydration of propylene.

The production of tertiary butyl alcohol by the direct hydration of isobutene is also a well researched process. For instance, U.S. Pat. No. 3,328,471 (Krönig et al.) describes a process for performing this reaction through the use of sulfonated cation exchange resins produced from aromatic vinyl compounds. Another process which produces tertiary alcohols is described in U.S. Pat. No. 4,284,831 (Okumura et al.). These references also teach that the isobutene feed stream may contain other $C_4$ hydrocarbons, specifically isobutane and normal butylenes. The latter reference indicates some $C_3$ and $C_5$ hydrocarbons may be present. It also specifies that the olefins may be produced by the catalytic cracking of petroleum naphtha.

U.S. Pat. No. 4,307,257 (Sada et al.) describes a process for producing tertiary butyl alcohol from a $C_3$ to $C_5$ hydrocarbon mixture which contains isobutylene. The composition of the hydrocarbon admixture is closely defined to be a butane-butylene fraction from which butadiene has been removed by extraction. In the example provided, the feed contained 2 wt. % of hydrocarbons other than $C_4$ hydrocarbons. This reference also describes the process operation, operating conditions, and the recovery of tertiary butyl alcohol.

U.S. Pat. No. 3,849,082 (Kozlowski et al.) is pertinent for its description of an integrated process which produces both secondary and tertiary alcohols. These products are, however, made in different reaction zones, and there is no provision made within the process for the production of olefins or the selective recycling of various compounds.

U.S. Pat. No. 4,393,256 issued to the applicant describes a process for the indirect hydration of olefins, which may be charged to the process as an admixture of $C_2$–$C_4$ hydrocarbons. This process does not employ a dehydrogenation zone or separation facilities for the ejection or recycling of saturates.

The catalytic dehydrogenation of light paraffins is also a well developed process. It is described in some detail in U.S. Pat. Nos. 4,376,225 (Vora) and 4,381,417 (Vora et al.). It is also described in articles at page 171 of the April 1982 issue of *Hydrocarbon Processing* and at page 191 of the Nov. 10, 1980 issue of *The Oil and Gas Journal*. The latter reference is also pertinent for its illustration that it is known to combine dehydrogenation processes with other hydrocarbon conversion operations such as alkylation and etherification.

BRIEF SUMMARY OF THE INVENTION

The subject invention is a process for the production of isopropyl and tertiary butyl alcohols from a feed stream which comprises propane and isobutane or from a feed stream which comprises propane, propylene, isobutane, and isobutylene. This allows the coproduction of both alcohols using one hydration zone. In the preferred embodiment, a saturate feed stream is passed into a dehydrogenation zone, with the effluent of this zone entering a two-column fractionation system. Saturates in the hydration zone effluent are recycled to the dehydrogenation zone. In an alternative embodiment, no dehydrogenation zone is present in the process, and the feed comprises unsaturated hydrocarbons. In this embodiment, the saturated hydrocarbons are rejected as additional product streams.

The first embodiment of the invention may be broadly characterized as a process for the production of isopropanol and tertiary butyl alcohol which comprises the steps of passing a feed stream which comprises propane and isobutane into a dehydrogenation zone maintained at dehydrogenation conditions and thereby forming a dehydrogenation zone effluent stream which comprises propane, propylene, isobutane, and isobutylene; passing the dehydrogenation zone effluent stream into a separation zone and separating propane from the hydrocarbons which enter the separation zone and producing a first process stream, which is rich in propane, and a separation zone effluent stream which comprises propylene, isobutane, and isobutylene; passing the first process stream into the dehydrogenation zone; passing the separation zone effluent stream into a hydration zone maintained at hydration-promoting conditions and producing a second process stream, which comprises propylene and isobutane, and a hydration zone product stream which comprises isopropanol and tertiary butyl alcohol and is withdrawn from the process; passing the second process stream into a fractionation zone operated at fractionation conditions effective to separate the entering hydrocarbons into a net overhead stream, which is rich in $C_3$ hydrocarbons, and a net bottoms stream which comprises isobutane; passing the net overhead stream into the separation zone; and passing the net bottoms stream into the dehydrogenation zone.

BRIEF DESCRIPTION OF THE DRAWING

The drawing is a simplified schematic diagram illustrating several significantly different embodiments of the invention. This representation is not intended to limit the scope of the subject invention to these particular embodiments.

In the preferred embodiment, a saturate feed stream which contains mainly propane and isobutane enters the process through line 1 and is admixed with recycle streams from lines 2 and 3. This admixture flows through line 4 into a dehydrogenation zone 5 wherein propylene and isobutylene are produced. The dehydrogenation zone effluent, which contains both the product olefins and unconverted saturates, flows through line 6 into a first fractionation column 9. $C_3$ hydrocarbons from line 7 also enter this column. The hydrocarbons entering this column are separated into a first net overhead stream carried by line 10, which preferably is rich in propylene, and a first net bottoms stream carried by line 11.

The first net bottoms stream is passed into a second fractionation column 12, which separates the entering hydrocarbons into a second net overhead stream, which is rich in propane, removed through line 2, and a second net bottoms stream carried by line 13. Isobutylene produced in the dehydrogenation zone is concentrated into the second net bottoms stream. This stream is combined with the first net overhead stream and passed through line 14 into the hydration zone 15. Water from line 8 combines with some of the olefinic hydrocarbons to produce isopropanol and tertiary butyl alcohol. These products are removed together as a product stream carried by line 16. The remaining hydrocarbons, which include propane, propylene, isobutane and isobutylene, leave the hydration zone as the recycle stream carried by line 17. This effluent stream is passed into a third fractionation column 18 in which it is split into a third net bottoms stream, which is rich in isobutane, and a third net overhead stream, which is rich in $C_3$ hydrocarbons. In this manner, isobutane is recycled through line 3 for dehydrogenation while propylene is recycled via line 7.

In a first alternative embodiment, an olefin-containing second feed stream carried by line 19 is also charged to the process. The olefins in this stream supplement those made in the dehydrogenation zone 5. Paraffins present in this supplemental feed stream are recycled to the dehydrogenation zone. In a second alternative embodiment, the only feed stream to the process is that charged through line 19. In a third alternative embodiment, the dehydrogenation zone 5 is not employed and only the olefin-containing feed of line 19 enters the process. The saturates which enter the process are rejected as additional product streams, with propane being discharged via line 21 and isobutane and any heavier hydrocarbons being discharged via line 20. Lines 20 and 21 are optional when a dehydrogenation zone is present.

DETAILED DESCRIPTION

Lower molecular weight alcohols are valuable and widely used industrial chemicals. For instance, isopropyl alcohol may be used as a solvent in coatings, inks and adhesives, as an antibacterial agent, and in cosmetics or as a feedstock in the production of other chemicals such as acetone. Tertiary butyl alcohol is also useful alone or as a feed compound in the production of other useful chemicals. Both of these alcohols are also used in increasing amounts in motor fuels due to their excellent octane number and freeze point characteristics and are also used as a cosolvent for methanol in various fuels. Besides having utility by producing these useful compounds, hydration processes have been described as suitable for the conversion of large amounts of excess light hydrocarbons into the less volatile compounds. The lower vapor pressure of alcohols compared to the corresponding olefins makes them easier and safer to transport as liquids. The production of alcohols is therefore being considered as a first step in the transportation of large amounts of light hydrocarbons by ship or similar tankage forms of transport.

It is an objective of the subject invention to provide a process for the production of lower aliphatic alcohols. It is also an objective of the subject invention to provide an integrated process for the production of both isopropanol and tertiary butyl alcohol from propane and isobutane. It is a specific objective of the invention to provide a process which provides significant conversion to both of these products utilizing a single hydration zone.

The feed hydrocarbons which are charged to the subject process may be characterized as the necessary precursors to the desired alcohols. Therefore, if the embodiment of the invention being practiced includes a dehydrogenation zone, then the feed stream need only contain propane and isobutane. Alternatively, two separate feed streams may be charged to the process, with a saturate feed stream entering the dehydrogenation zone and an olefin-containing second feed stream entering the fractionation zone. In this instance, the second feed stream need not contain either propylene or isobutylene. If the embodiment of the invention being practiced does not contain a dehydrogenation zone, then the feed stream(s) must contain propylene and isobutylene. It is preferred that the feed stream contains over 25 mole percent olefins in this instance.

The feed hydrocarbons may be obtained from conventional sources such as the effluent streams of catalytic cracking units or from natural gas. Gases from these sources will be separated, as by fractional distillation, to produce feed streams containing the desired hydrocarbons. When a dehydrogenation zone is present in the process, it is preferred that feed stream(s) contain less than 5, and more preferably less than 2, mole percent of $C_4$ straight chain hydrocarbons. Normal butylenes will be converted secondary alcohols in the hydration zone, and the production of these alcohols in the process is presently not desired. If there is no dehydrogenation zone employed in the process, then the passage of butanes into the process is acceptable as they will pass through the hydration zone unaffected. The butanes can be drawn off as a portion of the bottoms stream of the third fractionation column. In this instance, it is still preferred that significant amounts of normal olefins are not passed into the process. It is also preferred that the feed stream(s) to the process does not contain a significant amount of butadiene.

The following description will be based on the assumption that a dehydrogenation zone is present in the process flow. The separation and hydration zones of those embodiments in which it is not present operate in a very similar manner to when it is present. This description therefore should serve as adequate guidance to the intended design and operation of any of the various embodiments.

The saturate feed stream and two recycle streams described below are passed into the dehydrogenation zone. This zone will contain a reaction zone and associated auxiliary process equipment such as condensers and a vapor-liquid separator which receives the partially condensed reactor effluent stream. The dehydrogenation zone preferably also contains at least one fractionation column operated as a light ends stripping column. This column is designed and operated to eliminate all ethane and lighter boiling components from the net dehydrogenation zone effluent stream. A hydrogen-rich gas stream is separated from the liquid condensed from the reactor effluent. A portion of this gas will normally be recycled and the remainder will be drawn off as a net hydrogen product gas stream. This gas stream will contain a mixture of the various olefins produced in the dehydrogenation zone at a concentration set by the separation conditions. The reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887; and 3,856,662.

The particular dehydrogenation conditions employed within the reaction zone may vary depending on such factors as catalyst activity and the desired conversion. The reaction zone conditions normally employed for this dehydrogenation reaction include a temperature of from about 500° to 700° C., a pressure of from 0.5 to about 10 atmospheres and a liquid hourly space velocity of about 1 to 8. The preferred operating temperature will be within the range of from about 600° to 680° C. and the preferred operating pressure is about 0.5 to 2 atmospheres.

The preferred dehydrogenation catalyst is comprised of a platinum group component, a tin component, and an alkali metal component with a porous inorganic carrier material. Other catalytic compositions may be used within this zone if desired.

It is preferred that the porous carrier material is an absorptive high surface area support having a surface area of about 25 to about 500 $m^2/g$. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, etc.; crystalline aluminosilicates such as naturally occurring or synthetically prepared mordenite or a combination of one or more of these materials. The preferred porous carrier material is a refractory inorganic oxide with the best results being obtained with an alumina carrier material. The crystalline alumina, such as gamma alumina, give the best results. In general, the preferred catalysts will have a gamma alumina carrier which is in the form of spherical particles having a relatively small diameter on the order of about 1/16-inch.

The preferred alumina carrier material may be prepared in any suitable manner. For example, the alumina carrier may be prepared by adding a suitable alkaline reagent, such as ammonium hydroxide to a salt of alumina such as aluminum chloride in an amount sufficient to form an aluminum hydroxide gel which upon drying and calcining is converted to alumina. It is particularly preferred that alumina spheres are manufactured by the well known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics.

The resulting pellets are then washed and dried at relatively low temperatures of about 150° to about 200° C. and calcined at a temperature of about 450° to about 700° C. for a period of about 1 to about 20 hours. See the teachings of U.S. Pat. Nos. 2,620,314; 4,250,058; and 4,273,735 for additional details on the preparation of base materials by the oil dropping method.

The preferred dehydrogenation catalyst also contains a platinum group component. Of the platinum group metals, which include palladium, rhodium, ruthenium, osmium, and iridium, the use of platinum is preferred with palladium being the next preferred metal. The platinum group component may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt. % of the final catalytic composite, calculated on an elemental basis. It is preferred that the platinum content of the catalyst is between about 0.1 and 1 wt. %. The platinum group component may be incorporated into the catalytic composite in any suitable manner such as by coprecipitation or cogelation with the preferred carrier material, or by ion exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the preferred catalyst should constitute about 0.01 to about 5 wt. % of the final composite, calculated on an elemental basis, although substantially higher amounts of tin may be utilized in some cases. Best results are often obtained with about 0.1 to about 1 wt. % tin. It is preferred that the atomic ratio of tin to platinum is between 1:1 and about 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitating it during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred dehydrogenation catalyst normally contains less than 0.5 wt. % halogen and preferably less than 0.1 wt. % halogen. However, some halogen, specifically chlorine, at or above these concentrations may be tolerated in some instances and could at times even be preferred as in the case of isobutane. The preferred catalyst contains an alkali metal component chosen from cesium, rubidium, potassium, sodium, and lithium. The preferred alkali metal is normally chosen from lithium and potassium, with potassium being preferred for isobutane-containing feedstocks. The concentration of the alkali metal may range from between 0.1 and 3.5 wt. % but is preferably between 0.5 and about 3 wt. % calculated on an elemental basis.

The net effluent of the dehydrogenation zone will contain a mixture of unconverted feed hydrocarbons and product olefins. This stream is passed into a separation zone which preferably comprises two fractional distillation columns as shown on the Drawing. Other separation techniques such as absorption and other types of distillation apparatus may be used if desired in place of the preferred trayed columns. The dehydrogenation zone effluent stream is therefore passed into a first fractionation column either separately or in admixture with a recycle stream and any additional olefin-containing feed material. The function of the first column is to produce an overhead stream which contains a great majority, preferably over 85 mole percent, of the propylene which enters this column. This first overhead stream will also contain some propane. A very sharp split at this point between propane and propylene is not necessary and would consume excessive capital and operational utilities. However, it is preferred that the first overhead stream contains over 90 mole percent propylene. The net bottoms stream of the first column will contain the other hydrocarbons fed to this column. It will therefore contain propane, isobutane, and isobutylene.

The net bottoms stream of the first column is charged to an intermediate point of a second fractionation column. Any olefin-containing feed stream which contains very little propylene could also be charged to this column. The function of the second column is to separate propane from the entering hydrocarbons to thereby produce a second net overhead stream which is rich in propane. This overhead stream should contain as little propylene as is commercially practical since propylene has deleterious effects on the activity of the preferred dehydrogenation catalyst. Further, when a dehydrogenation zone is not employed, it is desired to minimize the escape of propylene in this stream, which is discharged from the process. This is to increase isopropyl alcohol production and to minimize the olefin content of the discharged LPG. The second overhead stream should therefore contain less than 5 mole percent propylene. This stream preferably comprises at least 95 mole percent propane. The net bottoms stream of the second column should contain essentially all of the isobutylene and isobutane which enters this column. The isobutylene concentration of this stream may be between 30 and 50 mole percent. The bottoms stream of the second column is passed into the hydration zone. This may be as a separate hydration zone feed stream but is preferably done by admixture with the overhead stream of the first fractionation column. The combination of these two streams is also referred to herein as the separation zone effluent. This generic characterization is intended to also refer to streams produced by absorptive separation techniques or other separation systems which produce a single olefin-rich effluent stream.

The chemical compounds intentionally charged to the hydration zone are water and the olefinic hydrocarbons which are concentrated in the separation zone. The olefinic hydrocarbons will normally be admixed with paraffin hydrocarbons which essentially pass through the hydration zone as inerts. It is preferred that over 60 mole percent of the hydrocarbons fed to the hydration zone are olefins. More preferably, over 70 mole percent of these hydrocarbons are made up of propylene and isobutylene.

The feed olefins are admixed with water and passed into the hydration zone. Preferably, the hydration zone reactor comprises a single vertical tower-like vessel having suspended therein one or more beds of the solid hydration catalyst. Preferably, the reactor is operated as a trickle bed-type reactor with the olefin-water feed admixture entering the top of the reactor and passing downward through the catalyst to a void volume located in the lower portion of the reactor vessel. This void volume is preferably employed as a vapor-liquid separation zone. Vapors comprising the inert paraffin and any residual olefinic hydrocarbon may be withdrawn on a pressure control basis from this void volume. An aqueous phase collects in the bottom of the void volume and may be withdrawn on level control. The hydration reaction is exothermic, and it is therefore preferred that additional amounts of relatively low temperature water are injected into the descending reactants at several points along the height of the catalyst-containing zone within the reaction vessel.

The olefin-water feed admixture to the reaction vessel should contain at least a molar excess of water over that which is stoichiometrically required for the hydration reaction. The water concentration within the reaction zone is an important variable in the process. It is preferred that the molar ratio of water to entering olefinic hydrocarbon is between about 5:1 and 20:1. More preferably, this ratio is between about 8:1 and about 20:1. Each mole of the olefinic hydrocarbon charged to the reaction vessel therefore requires the addition of from about 8 to about 20 moles of water. Since only a small proportion of this water is consumed in the hydration reaction, the product alcohol is withdrawn from the hydration reaction vessel as a part of a relatively dilute aqueous alcohol solution.

The hydration conditions which are suitable for the subject process include a pressure of from about 60 to about 200 atmospheres. Preferably, the hydration reactor is maintained at a pressure of from about 80 to about 125 atmospheres absolute. The hydration reaction zone is preferably operated at a temperature between about 135° and about 160° C. The hydration of butylene occurs rapidly at milder conditions than the hydration of propylene. These conditions are therefore those which are preferred for the conversion of propylene to isopropyl alcohol. In this instance, it has been characterized as maintaining the propylene as a supercritical gas and the water as a liquid. Other conditions may be preferred with different catalysts other than the preferred resin-type catalyst. The rate of water flow through the catalyst bed is preferably between about 1 and about 40 and more preferably between about 5 and about 25 moles of water per $cm^2$ of cross-sectional area per hour. The liquid hourly space velocity of the entering olefinic hydrocarbon should be between about 0.1 and 1.0.

As the subject invention basically relates to an overall process flow, it is not limited to any particular hydration catalyst. The subject process may therefore be employed utilizing the presently preferred catalyst or those which are the result of the continuing research effort in this area. It is preferred that a solid particulate catalyst is employed. The presently preferred hydration catalysts comprise an ion exchange resin. The preferred resins comprise a copolymer of styrene and divinylbenzene. It is further preferred that these copolymer resins are treated with a sulfur-containing acid to yield a highly acidic sulfonic acid-containing resin. In general, the catalyst should contain from about 0.2 to 1 sulfonic acid group per aromatic ring present in the resin. These catalysts may be further modified as by chlorination, fluorination, etc., which has been shown to yield improved high temperature stability. A particularly preferred resin of this nature is described in the previously referred to U.S. Pat. No. 4,340,769. Suitable catalysts are available from commercial sources.

The aqueous stream withdrawn as the hydration reactor effluent stream will contain an admixture of the product alcohol, water, any paraffinic hydrocarbons present in the feed stream, unreacted olefinic hydrocarbon, and the various possible reaction byproducts such as ethers and ketones. It is preferred that this admixture is subjected to one or more flash operations which generate a vapor phase comprising the more volatile components present in the effluent. This vapor phase will basically be an admixture of propane and propylene. These vapors may be passed directly into the third fractionation zone to recover the propylene. The product alcohol remains in the aqueous liquid phase portion withdrawn from the separation steps. Depending on the conditions desired for use within the hydration reaction zone, these flashing steps may be limited or eliminated. However, the use of one such flash separation is presently preferred.

The product alcohols are then preferably recovered from the remaining aqueous liquid discharged from the hydration reactor. The present technology depends on some form of fractional distillation or extractive distillation to recover the product alcohol from the aqueous liquid. This does not prevent the application of rapidly developing separation techniques such as the use of selectively permeable membranes or absorptive separation. The choice of the method employed to recover the alcohols will be influenced by the intended end use of the alcohols. The subject process may be used in the production of relatively high purity alcohol products. However, the invention is also highly suited for the production of fuel grade alcohols. When used for this purpose, the alcohols may contain significant amounts of by-products, up to 5 or possibly 10 wt. %, such as ethers and ketones. The product alcohols may also contain a small amount of water when used as motor fuel blending components. Water concentrations on the order of 0.5% are tolerable when the alcohol is used for this purpose. The separation facilities for the recovery of the alcohols may be located within the hydration zone, or the hydration zone product stream may comprise an aqueous admixture of both alcohols. The product stream should, however, contain the lowest olefinic hydrocarbon concentration which is commercially practical. The aqueous liquid produced by flashing the reactor effluent is therefore preferably passed into at least one fractionation column located within the hydration zone. The function of this column is to separate hydrocarbons from the aqueous material. These hydrocarbons, both paraffins and olefins, are thereby concentrated into a stream referred to herein as the hydration zone recycle stream or the second process stream. This stream is internally recycled within the process to increase olefin consumption.

The major components of the hydration zone recycle stream are propylene and isobutane. Propylene is not as easily hydrated as isobutylene and will therefore be present in the hydration reactor effluent. Isobutane is difficult to fractionate from isobutylene. It is therefore allowed to recycle through the process. It is separated from the isobutylene through isobutylene hydration prior to recycling to the dehydrogenation zone or rejection from the process. This recycle stream will also contain some propane. The hydration zone recycle stream is passed into a third fractionation zone. This zone also preferably comprises a single trayed column. The primary function of this column is to separate propylene from the entering hydrocarbons for the purpose set out above. The propylene is concentrated into a third net overhead stream passed into the first fractionation zone or the equivalent point of a separation zone. Propane entering this column may be allowed to exit as part of the bottoms stream and thereby recycled directly to the dehydrogenation zone or it may be removed overhead. Propane removed in the overhead is concentrated into the second net overhead stream as previously described. To minimize the cost of the column and the utilities cost of its operation, the third column may be designed and operated to perform a rather incomplete separation in which isobutane is removed overhead. The isobutane will then simply recycle through the other fractionation columns and the hydration zone. The net bottoms stream will then have a quite high isobutane concentration, assuming only minimal amounts of normal $C_4$ hydrocarbons enter the process. It is preferred that the net bottoms stream contains over 95 mole percent isobutane.

The preferred embodiment of the invention may be characterized as a process for the production of isopropanol and tertiary butyl alcohol which comprises the steps of passing a first feed stream which comprises propane and isobutane into a dehydrogenation zone maintained at dehydrogenation conditions and thereby forming a dehydrogenation zone effluent stream which comprises propane, propylene, isobutane, and isobutylene; passing the dehydrogenation zone effluent stream into a first fractionation zone maintained at fractionation conditions effective to separate the entering hydrocarbons into a first net overhead stream, which is rich in propylene, and a first net bottoms stream comprising propane, isobutane, and isobutylene; passing the first net bottoms stream into a second fractionation zone maintained at fractionation conditions effective to separate the entering hydrocarbons into a second net overhead stream, which is rich in propane, and a second net bottoms stream which comprises isobutane and isobutylene; passing at least a portion of the second net overhead stream into the dehydrogenation zone; passing the first net overhead stream and the second net bottoms stream into a hydration zone maintained at hydration-promoting conditions, and thereby producing a hydration zone product stream which comprises isopropanol and tertiary butyl alcohol and a hydration zone recycle stream which comprises propylene and isobutane; passing the hydration zone recycle stream into a third fractionation zone operated at fractionation conditions effective to separate the entering hydrocarbons into a third net overhead stream, which is rich in $C_3$ hydrocarbons, and a third net bottoms stream which comprises isobutane; passing the third net overhead stream into the first fractionation zone; and passing at least a portion of the third net bottoms stream into the dehydrogenation zone. The chemical compounds separated in these fractionation zones are common chemicals having well known thermodynamic characteristics. They are separated by fractional distillation in a large number of commercial industrial units. Those skilled in the art therefore should require no further direction as to the proper design and operation of these fractionation facilities.

The subject invention may also be practiced without the presence of a dehydrogenation zone. This is not preferred as it limits alcohol production, but this embodiment could be highly useful when a suitable olefin source is available. One version of this embodiment may be characterized as a process for the production of isopropanol and tertiary butyl alcohol which comprises the steps of passing a first feed stream which comprises propane, propylene, isobutylene, and isobutane into a first fractionation zone maintained at fractionation conditions effective to separate the entering hydrocarbons into a first net overhead stream, which is rich in propylene, and a first net bottoms stream comprising propane, isobutane, and isobutylene; passing the first net bottoms stream into a second fractionation zone maintained at fractionation conditions effective to separate the entering hydrocarbons into a second net overhead stream, which is rich in propane, and a second net bottoms stream which comprises isobutane and isobutylene; passing the first net overhead stream and the second net bottoms stream into a hydration zone maintained at hydration-promoting conditions, and thereby producing a hydration zone product stream which comprises isopropanol and tertiary butyl alcohol and a hydration zone recycle stream which comprises propylene and isobutane; passing the hydration zone recycle stream into a third fractionation zone operated at fractionation conditions effective to separate the entering hydrocarbons into a third net overhead stream, which is rich in $C_3$ hydrocarbons, and a third net bottoms stream which comprises isobutane; passing the third net overhead stream into the first fractionation zone; and removing at least a portion of the first net overhead stream and the third net bottoms stream from the process. The first net overhead stream and the third net bottoms stream remove the essentially inert saturates. Portions of both or either of these streams may also be withdrawn from the process when a dehydrogenation zone is present. This may be done to adjust the relative production of the two product alcohols. The withdrawal of a small portion of the third net bottoms stream may also be desired to control or reduce the buildup of normal $C_4$ hydrocarbons in the process.

I claim as my invention:

1. A process for the production of isopropanol and tertiary butyl alcohol which comprises the steps of:
   (a) passing a first feed stream which comprises propane and isobutane into a dehydrogenation zone maintained at dehydrogenation conditions and thereby forming a dehydrogenation zone effluent stream which comprises propane, propylene, isobutane, and isobutylene;
   (b) passing the dehydrogenation zone effluent stream into a separation zone and separating propane from the hydrocarbons which enter the separation zone and producing a first process stream, which is rich in propane, and a separation zone effluent stream which comprises propylene, isobutane, and isobutylene;

(c) passing the first process stream into the dehydrogenation zone;

(d) passing the separation zone effluent stream into a hydration zone maintained at hydration-promoting conditions and producing a second process stream, which comprises propylene and isobutane, and a hydration zone product stream which comprises isopropanol and tertiary butyl alcohol and is withdrawn from the process;

(e) passing the second process stream into a fractionation zone operated at fractionation conditions effective to separate the entering hydrocarbons into a net overhead stream, which is rich in $C_3$ hydrocarbons, and a net bottoms stream which comprises isobutane;

(f) passing the net overhead stream into the separation zone; and (g) passing the net bottoms stream into the dehydrogenation zone.

2. The process of claim 1 further characterized in that the net bottoms stream contains less than 2 mole percent propylene.

3. The process of claim 2 further characterized in that the hydration zone contains a catalyst which comprises a cation exchange resin.

4. The process of claim 3 further characterized in that the dehydrogenation zone contains a solid catalyst which comprises a Group VIII metal.

5. The process of claim 1 further characterized in that a second feed stream, which comprises propylene or isobutylene, is passed into the separation zone.

6. A process for the production of isopropanol and tertiary butyl alcohol which comprises the steps of:

(a) passing a first feed stream which comprises propane and isobutane into a dehydrogenation zone maintained at dehydrogenation conditions and thereby forming a dehydrogenation zone effluent stream which comprises propane, propylene, isobutane, and isobutylene;

(b) passing the dehydrogenation zone effluent stream into a first fractionation zone maintained at fractionation conditions effective to separate the entering hydrocarbons into a first net overhead stream, which is rich in propylene, and a first net bottoms stream comprising propane, isobutane, and isobutylene;

(c) passing the first net bottoms stream into a second fractionation zone maintained at fractionation conditions effective to separate the entering hydrocarbons into a second net overhead stream, which is rich in propane, and a second net bottoms stream which comprises isobutane and isobutylene;

(d) passing at least a portion of the second net overhead stream into the dehydrogenation zone;

(e) passing the first net overhead stream and the second net bottoms stream into a hydration zone maintained at hydration-promoting conditions, and thereby producing a hydration zone product stream which comprises isopropanol and tertiary butyl alcohol and a hydration zone recycle stream which comprises propylene and isobutane;

(f) passing the hydration zone recycle stream into a third fractionation zone operated at fractionation conditions effective to separate the entering hydrocarbons into a third net overhead stream, which is rich in $C_3$ hydrocarbons, and a third net bottoms stream which comprises isobutane;

(g) passing the third net overhead stream into the first fractionation zone; and (h) passing at least a portion of the third net bottoms stream into the dehydrogenation zone.

7. The process of claim 6 further characterized in that a second feed stream which comprises propylene and/or isobutylene is passed into the first fractionation zone.

8. The process of claim 6 further characterized in that the third net bottoms stream contains essentially no propylene.

9. The process of claim 8 further characterized in that the first net overhead stream and the hydration zone recycle stream also comprise propane.

10. The process of claim 6 further characterized in that the hydration zone contains a solid hydration catalyst which comprises a cation exchange resin.

11. The process of claim 10 further characterized in that the hydration catalyst comprises a sulfonated styrene-divinyl benzene copolymer resin.

12. The process of claim 6 further characterized in that a second feed stream, which comprises propylene or isobutylene, is passed into the first fractionation column.

13. A process for the production of isopropanol and tertiary butyl alcohol which comprises the steps of:

(a) passing a feed stream which comprises propane, propylene, isobutylene, and isobutane into a first fractionation zone maintained at fractionation conditions effective to separate the entering hydrocarbons into a first net overhead stream, which is rich in propylene, and a first net bottoms stream comprising propane, isobutane, and isobutylene;

(b) passing the first net bottoms stream into a second fractionation zone maintained at fractionation conditions effective to separate the entering hydrocarbons into a second net overhead stream, which is rich in propane, and a second net bottoms stream which comprises isobutane and isobutylene;

(c) passing the first net overhead stream and the second net bottoms stream into a hydration zone maintained at hydration-promoting conditions, and thereby producing a hydration zone product stream which comprises isopropanol and tertiary butyl alcohdl and a hydration zone recycle stream which comprises propylene and isobu- tane;

(d) passing the hydration zone recycle stream into a third fractionation zone operated at fractionation conditions effective to separate the entering hydrocarbons into a third net overhead stream, which is rich in $C_3$ hydrocarbons, and a third net bottoms stream which comprises isobutane;

(e) passing the third net overhead stream into the first fractionation zone; and (f) removing at least a portion of the first net overhead stream and the third net bottoms stream from the process.

14. The process of claim 13 further characterized in that the hydration zone contains a solid hydration catalyst comprising a cation exchange resin.

15. A process for the production of isopropanol and tertiary butyl alcohol which comprises the steps of:

(a) passing a feed stream which comprises propane, propylene, isobutane, and isobutylene into a first fractionation zone maintained at fractionation conditions effective to separate the entering hydrocarbons into a first net overhead stream, which is rich in propylene, and a first net bottoms stream comprising propane, isobutane, and isobutylene;

(b) passing the first net bottoms stream into a second fractionation zone maintained at fractionation conditions effective to separate the entering hydrocarbons into a second net overhead stream, which is rich in propane, and a second net bottoms stream which comprises isobutane and isobutylene;

(c) passing the first net overhead stream and the second net bottoms stream into a hydration zone maintained at hydration-promoting conditions, and thereby producing a hydration zone product stream which comprises isopropanol and tertiary butyl alcohol and a hydration zone recycle stream which comprises propylene and isobutane;

(d) passing the hydration zone recycle stream into a third fractionation zone operated at fractionation conditions effective to separate the entering hydrocarbons into a third net overhead stream, which is rich in $C_3$ hydrocarbons, and a third net bottoms stream which comprises isobutane;

(e) passing the third net overhead stream into the first fractionation zone;

(f) passing the second net overhead stream and the third net bottoms stream into a dehydrogenation zone maintained at dehydrogenation conditions and thereby forming a dehydrogenation zone effluent stream which comprises propane, propylene, isobutane, and isobutylene; and (g) passing the dehydrogenation zone effluent stream into the first fractionation column.

16. The process of claim 15 further characterized in that the third net bottoms stream contains less than 2 mole percent propylene.

17. The process of claim 16 further characterized in that the third net overhead stream comprises propane.

18. The process of claim 17 further characterized in that the first net overhead stream and the hydration zone recycle stream also comprise propane.

19. The process of claim 18 further characterized in that the hydration zone contains a solid hydration catalyst which comprises a cation exchange resin.

20. The process of claim 19 further characterized in that the hydration catalyst comprises a sulfonated styrene-divinyl benzene copolymer resin.

* * * * *